United States Patent [19]

Brzezinski

[11] Patent Number: 5,482,843
[45] Date of Patent: Jan. 9, 1996

[54] ENZYME OF USE IN CHITOSAN HYDROLYSIS

[75] Inventor: Ryszard Brzezinski, Sherbrooke, Canada

[73] Assignee: Universite De Sherbrooke, Canada

[21] Appl. No.: 988,260

[22] Filed: Dec. 14, 1992

[51] Int. Cl.[6] .............................. C12N 9/42; C12N 15/56; C12P 19/26; C12P 19/04

[52] U.S. Cl. .......................... 435/84; 435/101; 435/209; 530/23.2

[58] Field of Search ............................ 435/209, 84, 101; 536/23.2

[56] References Cited

PUBLICATIONS

D. Fink et al. "Cloning and Expression in Streptomyces . . ." Biotechnology Letters. 13(12) 845–850 (Dec. 1991).
I. Boucher et al. "Purification and Characterization of a . . ." Applied Microbiol. and Biotechnol. 38(2) 188–193 (Nov. 1992).
Denis, F., et al. (1992). Gene 111: 115.
Denis, F., et al., (1991). FEMS Microbiol. Lett. 81: 261–264.
Neugebauer, E., et al. (1991). Arch. Microbiol. 156: 192–197.
Pelletier, A., et al. (1990). Appl. Environ. Microbiol. 56(4): 844–848.
Price, J. S., et al. (1975). J. Bacteriol. 124(3): 1574–1585.
Sakai, K., et al. (1991). Biochim. Biophys. Acta 1079: 65–72.

*Primary Examiner*—Charles L. Patterson, Jr.
*Assistant Examiner*—Rebecca Prouty
*Attorney, Agent, or Firm*—Cushman Darby & Cushman

[57] ABSTRACT

The present invention relates to a naturally occuring, isolated and characterized microorganism producing hydrolase enzyme, specifically, chitosanase; chitosanase isolated thereof; the nucleic acid sequence of the portion of the gene encoding this chitosanase; complete amino acid sequence of this chitosanase; hybrid plasmids containing the related gene; host microorganisms transformed with the plasmids; recombinant microorganisms overexpressing the enzyme; and to enzymatic treatment of chitosan with the aforementioned enzyme resulting in molecular weight decrease, viscosity decrease and increase of solubility of chitosan in water.

9 Claims, 6 Drawing Sheets

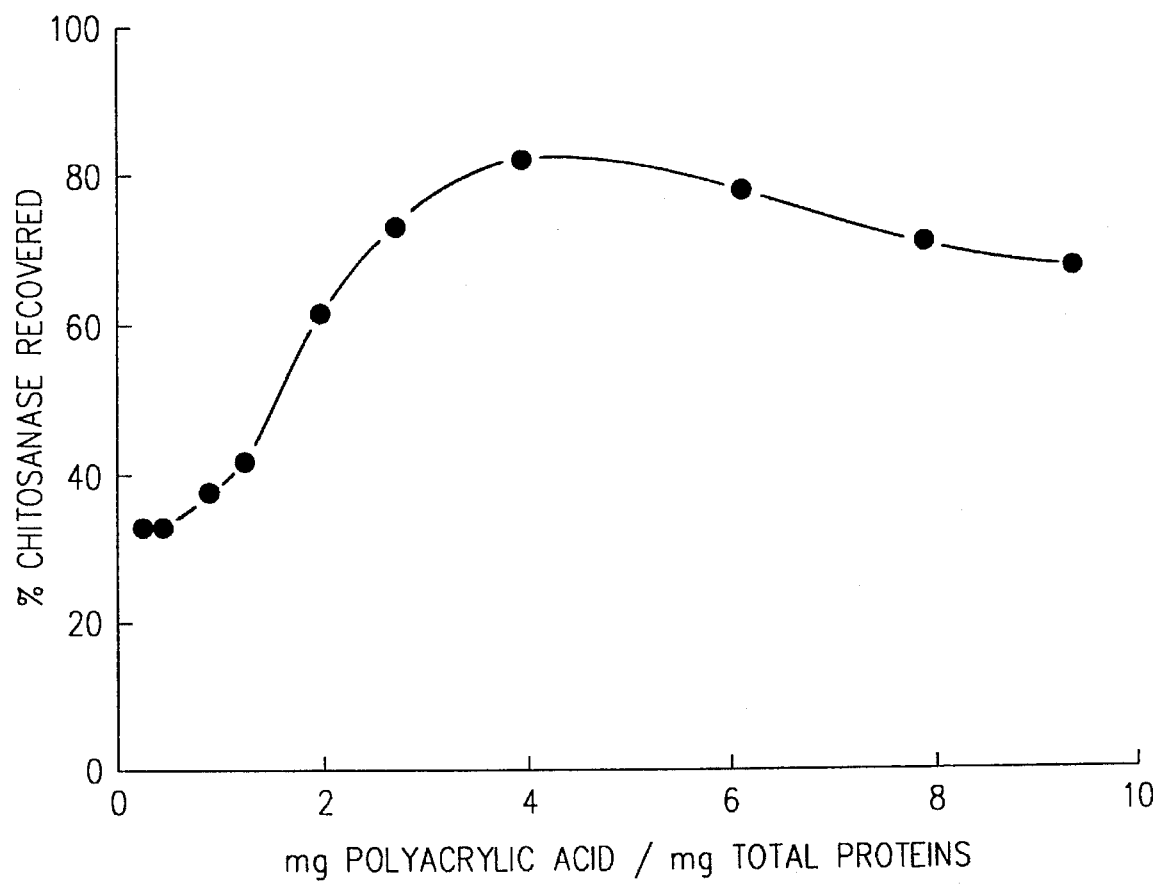
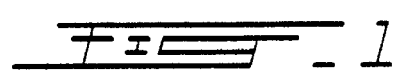
PRECIPITATION OF N174 CHITOSANASE WITH
VARIOUS LEVELS OF POLYACRYLIC ACID AT pH 4.5

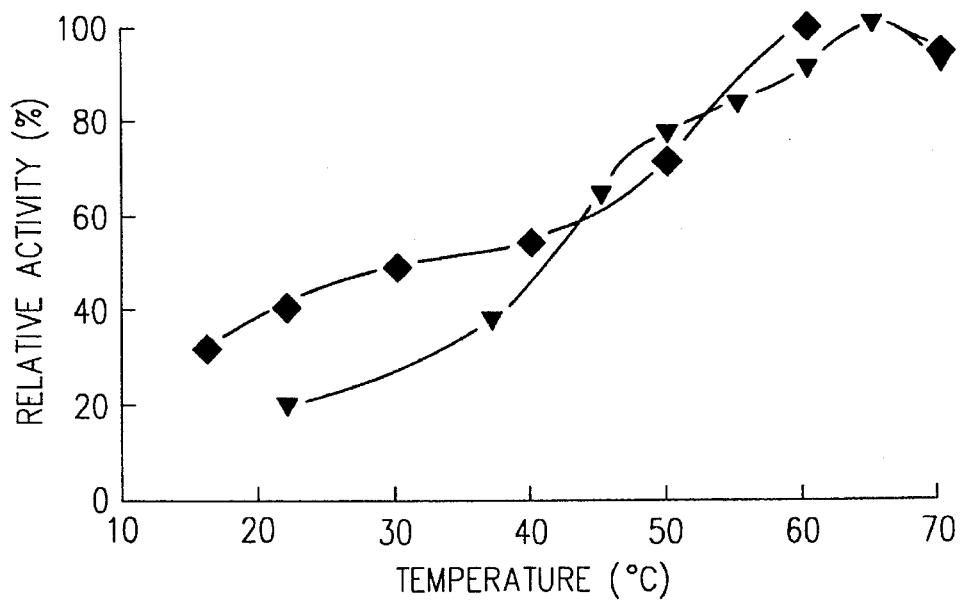
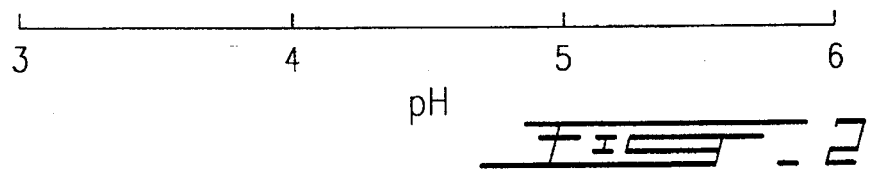
FIG. 2
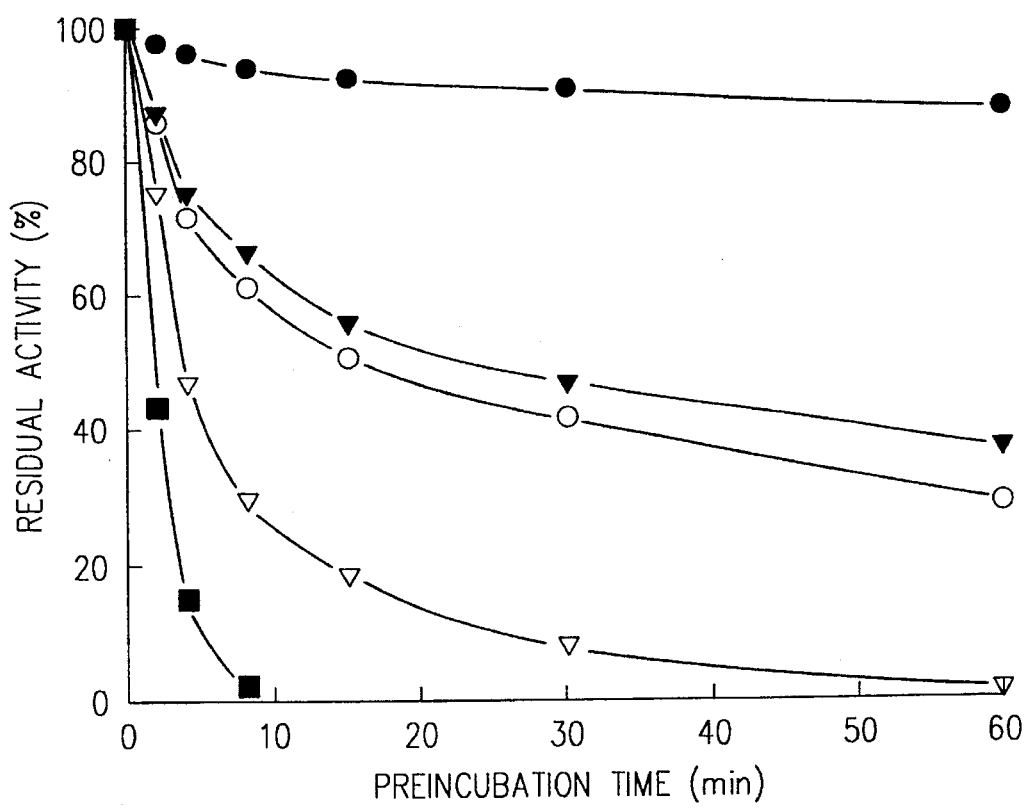
FIG. 3

```
    BamHI
    GGATCCGTCCGGGGGGGGCCCTCTGCGTGTCCGGGCTCCTCTGCGTGAGCCGGAGTCTGACGGTCCGTCACTTCGGTGGCGGATCGTT
1   ----+----+----+----+----+----+----+----+----+----+----+----+----+----+----+----+----+----+  90
    CCTAGGCAGGCCCCCCCCCGGGAGAGACGCACAGGCCCGAGGAGACGCACTCGGCCTCAGACTGCCAGGCAGTGAAGCCACCGCCTAGCAA
    SphI
    GGCATGCGGCGCGGGTCAGGGATTTGGGGCGGGGCCCTTGCGGAGGGCCGGGAGGGGGCGCTTGAATCGGTTAGGAAAGTTCCTAACTCTC
91  ----+----+----+----+----+----+----+----+----+----+----+----+----+----+----+----+----+----+  180
                                               NdeI
    TCTGCGGGCACCCCATGCCAGCGACAGAAGACGGAGCGTCATATGCACTCGCAGCACCGGACCGCACGGCATCGCCCTGGCCGTCGTCC
181 ----+----+----+----+----+----+----+----+----+----+----+----+----+----+----+----+----+----+  270
                             M  H  S  Q  H  R  T  A  R  I  A  L  A  V  V  L
                                                              BglI            NaeI
    TCACCGGCGATACCCGGCACTCGGCTCGCCACCGCCCGGAGTCGGCTACGCCTCCACTCAGGCGAGCACCGCCGTCAAGGCCGGTGCCGGCCTCG
271 ----+----+----+----+----+----+----+----+----+----+----+----+----+----+----+----+----+----+  360
     T  A  I  P  A  S  L  A  T  A  G  V  G  Y  A  S  T  Q  A  S  T  A  V  K  A  G  A  G  L  D
                                                    SacI
    ACGATCCCCACAAGAAGGAGATCGCGATGGAGCTCGTCTCCAGCGCCGAGAACTCCTCCCTCGACTGGAAGGCCCAGTACAAGTACATCG
361 ----+----+----+----+----+----+----+----+----+----+----+----+----+----+----+----+----+----+  450
     D  P  H  K  K  E  I  A  M  E  L  V  S  S  A  E  N  S  S  L  D  W  K  A  Q  Y  K  Y  I  E
                SacII
    AGGACATCGGTGACGGCCGCGGCTACACCGGCGGCATCATCGGCTTCTGTTCCGGGACCGGGGACATGCTGGAACTCGTCCAGCACTACA
451 ----+----+----+----+----+----+----+----+----+----+----+----+----+----+----+----+----+----+  540
     D  I  G  D  G  R  G  Y  T  G  G  I  I  G  F  C  S  G  T  G  D  M  L  E  L  V  Q  H  Y  T
```

FIG. 5A

```
541 CCGACCTGGAGCCCGGCAACATCCTCGCCAAGTACCTGCCCGCGCTGAAGAAGGTCAACGGCTCGGCCTCCCACTCCGGGCTCGGCACCC 630
     D  L  E  P  G  N  I  L  A  K  Y  L  P  A  L  K  K  V  N  G  S  A  S  H  S  G  L  G  T  P

631 CGTTCACCAAGGACTGGGCGACCGCCGCCAAGGACACCGTCTTCCAGCAGGCCCAGAACGACGAGCGCGACCGGGTCTACTTCGACCCGG 720
     F  T  K  D  W  A  T  A  A  K  D  T  V  F  Q  Q  A  Q  N  D  E  R  D  R  V  Y  F  D  P  A

721 CCGTCAGCAGGCCAAGGCCGACGGCCTGCGCGCGCTGGGCCAGTTCGCCTACTACGACGCCATCGTGATGCACGGCCCCGGCAACGACC 810
     V  S  Q  A  K  A  D  G  L  R  A  L  G  Q  F  A  Y  Y  D  A  I  V  M  H  G  P  G  N  D  P

811 CGACCAGCTTCGGTGGCATCCGCAAGACCGCCATGAAGAAGGCCAGGACCCCGCCAGGGGCGGCGACGAGACCACCTACCTCAACGCCT 900
     T  S  F  G  G  I  R  K  T  A  M  K  K  A  R  T  P  A  Q  G  G  D  E  T  T  Y  L  N  A  F
                                     BglI
901 TCCTGGACGCCCGCAAGGCCGCCATGCTCACCGAGGCCGCGCACGACGACACCAGCCGCGTGGACACCGAGCAGCGGGTCTTCCTGAAGG 990
     L  D  A  R  K  A  A  M  L  T  E  A  A  H  D  D  T  S  R  V  D  T  E  Q  R  V  F  L  K  A
```

FIG. 5B

```
         NaeI                                   PvuII    NaeI
      CCGGCAACCTCGACCTCAACCCGCCGCTGAAGTGGAAGACCTACGGGGACCCGTACGTCATCAACAGCTGAGCCGGCTCGTCCCGGTGC
 991  ----+---------+---------+---------+---------+---------+---------+---------+---------+ 1080
       G  N  L  D  L  N  P  P  L  K  W  K  T  Y  G  D  P  Y  V  I  N  S  *

SmaI                        BglI
      GGCAGCGCCACCACCCGGCGCACGGCCCGGGATCGGCCGGAGGCCAGCTCGGACCTGGTTCGGGGCTGTCCGGCC
1081  ----+---------+---------+---------+---------+---------+---------+---------+ 1170

CGCTGCGGTGTTCTGCGGCCTGTCTGTTCCGGTCTGTTCCGGCCACTCGAAAATGTCGGGCGAGTGCCGGGGTGCCCGTAGCGTGGTCCGCC
1171  ----+---------+---------+---------+---------+---------+---------+---------+---------+ 1260

ATGACGCCTCCCTCCCGTACCGCCTACGACGGCGATGAGCGCACGCAGTTGATCGCCTGCTGGACATGCAGCGGGCGGTCGTC
1261  ----+---------+---------+---------+---------+---------+---------+---------+ 1350

CACTGGAAGTGCGACGGACTGTCCGGGAGGACGCCCACCGGGTGGTGATCCCGACCTCGCCCCTGATGACTGCGGCCGGCTGGTCTCC
1351  ----+---------+---------+---------+---------+---------+---------+---------+ 1440

CATCTGGGGTCGAGCACTGCTGGTTCGAGGTCATGCTGACGGGGCCCCGCGACCGGACCGCAGTTCGACGAGAGCATCGAGGAC
1441  ----+---------+---------+---------+---------+---------+---------+---------+ 1530

PstI
      GCGGACATGCGGGTGGAGGGCGTCCCGCTGGAGGCGACTGCTGCAG
1531  ----+---------+---------+---------+---- 1575
```

FIG. 5C

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 17 amino acids
        ( B ) TYPE: amino acid
        ( D ) TOPOLOGY: Unknown ( i i ) MOLECULE TYPE: Peptide ( v ) FRAGMENT TYPE: N-terminal fragment of chitosanase ( v i ) ORIGINAL SOURCE: Streptomyces N174

( x i ) SEQUENCE DESCRIPTION: SEQ ID NO: 1:

Ala Gly Ala Gly Leu Asp Asp Pro His Lys
                      5                     10

Lys Glu Ile Ala Met Glu Leu
                      15

( 2 ) INFORMATION FOR SEQ ID NO: 2:

( i ) SEQUENCE CHARACTERISTICS:

(A) LENGTH: 1575 base pairs
(B) TYPE: nucleic acid
(C) STRANDEDNESS: double
(D) TOPOLOGY: linear (ii) MOLECULE TYPE: cDNA to mRNA (vi) ORIGINAL SOURCE: Streptomyces N174

(xi) SEQUENCE DESCRIPTION: SEQ ID NO: 2:

| | | | | | |
|---|---|---|---|---|---|
| GGATCCGTC | CGGGCGGGGC | CCCTCTGCGT | GTCCGGGCTC | CTCTGCGTGA | 50 |
| GCCGGAGTCT | GACGGTCCGT | CACTTCGGTG | GCGGATCGTT | GGCATGCGCG | 100 |
| CGGTCAGGGA | TTTGGGGCGG | GGCCCTTGCG | GAGGGCCGGG | AGGGGGCGCT | 150 |
| TGAATCGGTT | AGGAAAGTTT | CCTAACTCTC | TCTGCGGGCA | CCCCCATGCC | 200 |
| CAGCGACAGA | AGACGGAGCG | TCATATGCAC | TCGCAGCACC | GGACCGCACG | 250 |
| CATCGCCCTG | GCCGTCGTCC | TCACCGCGAT | ACCCGCATCG | CTCGCCACCG | 300 |
| CCGGAGTCGG | CTACGCCTCC | ACTCAGGCGA | GCACCGCCGT | CAAGGCCGGT | 350 |
| GCCGGCCTCG | ACGATCCCCA | CAAGAAGGAG | ATCGCGATGG | AGCTCGTCTC | 400 |
| CAGCGCCGAG | AACTCCTCCC | TCGACTGGAA | GGCCCAGTAC | AAGTACATCG | 450 |
| AGGACATCGG | TGACGGCCGC | GGCTACACCG | GCGGCATCAT | CGGCTTCTGT | 500 |
| TCCGGGACCG | GCGACATGCT | GGAACTCGTC | CAGCACTACA | CCGACCTGGA | 550 |
| GCCCGGCAAC | ATCCTCGCCA | AGTACCTGCC | CGCGCTGAAG | AAGGTCAACG | 600 |
| GCTCGGCCTC | CCACTCCGGC | CTCGGCACCC | CGTTCACCAA | GGACTGGGCG | 650 |
| ACCGCCGCCA | AGGACACCGT | CTTCCAGCAG | GCCCAGAACG | ACGAGCGCGA | 700 |
| CCGGGTCTAC | TTCGACCCGG | CCGTCAGCCA | GGCGAAGGCC | GACGGCCTGC | 750 |
| GCGCGCTGGG | CCAGTTCGCC | TACTACGACG | CCATCGTGAT | GCACGGCCCC | 800 |
| GGCAACGACC | CGACCAGCTT | CGGTGGCATC | CGCAAGACCG | CCATGAAGAA | 850 |
| GGCCAGGACC | CCCGCCCAGG | GCGGCGACGA | GACCACCTAC | CTCAACGCCT | 900 |
| TCCTGGACGC | CCGCAAGGCC | GCCATGCTCA | CCGAGGCCGC | GCACGACGAC | 950 |
| ACCAGCCGCG | TGGACACCGA | GCAGCGGGTC | TTCCTGAAGG | CCGGCAACCT | 1000 |
| CGACCTCAAC | CCGCCGCTGA | AGTGGAAGAC | CTACGGGGAC | CCGTACGTCA | 1050 |
| TCAACAGCTG | AGCCGGCTCG | TCCCCGGTGC | GGCAGCGCAC | CACCCCGCCG | 1100 |
| CACCGGGGGC | ACGGCCCGGG | ATCGATCGGC | CGCCGAGGCC | AGCTCGGACC | 1150 |
| TGGTTCGGGG | CTGTCCGGCC | CGCTGCGGTG | TTCTGCGGCC | TGTTCCGGTC | 1200 |
| TGTTCCGGCC | ACTCGAAAAT | GTCGGGCGGA | GTGCGGCGGG | TGCCCGTAGC | 1250 |
| GTGGTCCGCC | ATGACGCCTC | CCTCCCGTAC | CCGCCCCGCC | TACGACGCCG | 1300 |
| TGAGCGCAC | GCAGTTGATC | GCCTGGCTGG | ACATGCAGCG | GCGGTCGTC | 1350 |
| CACTGGAAGT | GCGACGGACT | GTCCGGCGAG | GACGCCCACC | GGGTGGTGAT | 1400 |
| CCCGACCTCG | CCCCTGATGA | CTGCGGCCGG | GCTGGTCTCC | CATCTGCGGT | 1450 |
| GGGTCGAGCA | CTGCTGGTTC | GAGGTCATGC | TGACGGGGCG | CCCCGCGACC | 1500 |
| GGACCGCAGT | TCGACGAGAG | CATCGAGGAC | GCGGACATGC | GGGTGGAGGG | 1550 |
| CGTCCCGCTG | GAGCGACTGC | TGCAG | | | 1575 |

(2) INFORMATION FOR SEQ ID NO: 3:

(i) SEQUENCE CHARACTERISTICS:
(A) LENGTH: 278 amino acids
(B) TYPE: amino acid ( D ) TOPOLOGY: Unknown ( i i ) MOLECULE TYPE: Protein ( v i ) ORIGINAL SOURCE: Streptomyces N174

( x i ) SEQUENCE DESCRIPTION: SEQ ID NO: 3:

```
Met His Ser Gln His Arg Thr Ala Arg Ile
                  5                   10
Ala Leu Ala Val Val Leu Thr Ala Ile Pro
                 15                   20
Ala Ser Leu Ala Thr Ala Gly Val Gly Tyr
                 25                   30
Ala Ser Thr Gln Ala Ser Thr Ala Val Lys
                 35                   40
Ala Gly Ala Gly Leu Asp Asp Pro His Lys
                 45                   50
Lys Glu Ile Ala Met Glu Leu Val Ser Ser
                 55                   60
Ala Glu Asn Ser Ser Leu Asp Trp Lys Ala
                 65                   70
Gln Tyr Lys Tyr Ile Glu Asp Ile Gly Asp
                 75                   80
Gly Arg Gly Tyr Thr Gly Gly Ile Ile Gly
                 85                   90
Phe Cys Ser Gly Thr Gly Asp Met Leu Glu
                 95                  100
Leu Val Gln His Tyr Thr Asp Leu Glu Pro
                105                  110
Gly Asn Ile Leu Ala Lys Tyr Leu Pro Ala
                115                  120
Leu Lys Lys Val Asn Gly Ser Ala Ser His
                125                  130
Ser Gly Leu Gly Thr Pro Phe Thr Lys Asp
                135                  140
Trp Ala Thr Ala Ala Lys Asp Thr Val Phe
                145                  150
Gln Gln Ala Gln Asn Asp Glu Arg Asp Arg
                155                  160
Val Tyr Phe Asp Pro Ala Val Ser Gln Ala
                165                  170
Lys Ala Asp Gly Leu Arg Ala Leu Gly Gln
                175                  180
Phe Ala Tyr Tyr Asp Ala Ile Val Met His
                185                  190
Gly Pro Gly Asn Asp Pro Thr Ser Phe Gly
                195                  200
Gly Ile Arg Lys Thr Ala Met Lys Lys Ala
                205                  210
Arg Thr Pro Ala Gln Gly Gly Asp Glu Thr
                215                  220
Thr Tyr Leu Asn Ala Phe Leu Asp Ala Arg
                225                  230
Lys Ala Ala Met Leu Thr Glu Ala Ala His
                235                  240
```

```
            Asp  Asp  Thr  Ser  Arg  Val  Asp  Thr  Glu  Gln
                                 245                      250

Arg  Val  Phe  Leu  Lys  Ala  Gly  Asn  Leu  Asp
                                 255                      260

Leu  Asn  Pro  Pro  Leu  Lys  Trp  Lys  Thr  Tyr
                                 265                      270

Gly  Asp  Pro  Tyr  Val  Ile  Asn  Ser
                                 275
```

( 2 ) INFORMATION FOR SEQ ID NO: 4:

( i ) SEQUENCE CHARACTERISTICS:
        ( A ) LENGTH: 17 nucleotides
        ( B ) TYPE: nucleotide
        ( C ) STRANDEDNESS: single
        ( D ) TOPOLOGY: linear ( i i ) MOLECULE TYPE: Oligonucleotide
        ( A ) DESCRIPTION: Sequencing Primer ( v i ) ORIGINAL SOURCE: New England Biolabs ( x i ) SEQUENCE DESCRIPTION: SEQ ID NO: 4:
```
            GTA  AAA  CGA  CGG  CCA  GT                                 17
                                      25
```

ENZYME OF USE IN CHITOSAN HYDROLYSIS

FIELD OF THE INVENTION

The present invention relates to a naturally occuring, isolated and characterized microorganism producing hydrolase enzyme, specifically, chitosanase; chitosanase isolated thereof; the nucleic acid sequence of the portion of the gene encoding this chitosanase; complete amino acid sequence of this chitosanase; hybrid plasmids containing the related gene; host microorganisms transformed with the plasmids; recombinant microorganisms overexpressing the enzyme; and to enzymatic treatment of chitosan with the aforementioned enzyme resulting in molecular weight decrease, viscosity decrease and increase of solubility of chitosan in water.

BACKGROUND OF THE INVENTION

Chitin is a polymer of beta-1-4-N-acetyl-D-glucosamine found in fungal cell walls and crustacean shells. A common source of chitin consists of shells of marine invertebrates such as crabs and shrimps. Waste from industrial microbiological plants using fermentation methods with fungal organisms is another source of chitin.

Chitin is insoluble in water and most solvents. Its high hydrophobicity is the main reason of poor susceptibility to enzymatic hydrolysis. Enzymes that hydrolyse chitin—chitinases—have low specific activities and hydrolyse the polymer very slowly.

Chitin can be deacetylated partially or totally. Such a deacetylated polymer is called chitosan. In nature, chitosan is present only in cell walls of Zygomycetes, a group of phytopathogenic fungi. In contrast with chitin, chitosan is much less hydrophobic and is soluble in diluted acids (for instance in diluted HCl or in acetic acid). Because of its significant content of free amino groups, chitosan has a markedly cationic character and has a positive charge at most pHs. Enzymatic hydrolysis of chitosan is much easier than in the case of chitin.

Chitin deacetylation towards chitosan can be obtained by various methods. The most used method is that of alkaline treatment (Horowitz, S. T. et al., 1957). With this method, around 80% of deacetylation can be achieved without significant decrease of molecular weight. A more intense deacetylation cannot be obtained by this method without a simultaneous uncontrolled decrease of the degree of polymerization. A more promising method, but still under development, is deacetylation by a thermo-mechano-chemical treatment (Pelletier et al., 1990). This method allows a more careful control of the various characteristics of the final product (average degree of polymerisation and of deacetylation). Finally, a third method (Domard and Rinaudo, 1983) allows to obtain a totally deacetylated product. However, the cost of chemicals used in this method as well as their toxicity will probably limit the usefulness of this method to the laboratory scale.

High-molecular weight chitosan has many potential applications (reviewed by Sandford, 1989). Some applications are however typical of medium- or low-molecular weight chitosan (oligomeric chitosan). They include its exploitation as an antifungal agent; a seed coating for improving crop yield; an elicitor of anti-pathogenic natural reactions in plants; a hypocholesterolemic agent in animals; an accelerator of lactic acid bacteria breeding; and a moisture-retaining agent for lotions, hair tonics and other cosmetics. Furthermore, the anti-tumoral and immunostimulating properties of low-molecular weight chitosan are under active investigation in various laboratories and could lead to new important applications.

Hydrolysis of high-molecular weight chitosan, giving medium- or low-molecular weight chitosan can be achieved essentially by two methods. The chemical hydrolysis with strong acids (HCl or HF) is efficient but gives little possibility to control efficiently the molecular weight of the final product. The other method is enzymic hydrolysis with chitosanase. This enzyme hydrolyses beta-1,4-D-glucosaminic linkages of chitosan, reducing progressively the molecular weight of the polymer and giving low molecular weight oligomers as final hydrolysis product.

Reviewing the existing scientific and technical literature, we have found that the production of enzymes suitable for providing medium- or low-molecular weight chitosans through enzymatic treatment is often quite low in naturally occurring microorganisms and has to be enhanced in order to be commercially feasible.

Thus by molecular cloning and overexpression of a gene coding for chitosanase, improved production of this enzyme has been attained and found to be of value for chitosan hydrolysis.

The techniques of recombinant gene technology (gene cloning) are known and widely used. However, as yet, there is no known example of cloning of a chitosanase gene.

As a means for the production of an enzymic protein which: 1) exhibits a hydrolase activity, essentially a chitosanase activity; 2) is overproduced and present in a supernatant during the growth of a recombinant *Streptomyces lividans* microorganism, the present invention provided a gene system coding for such an enzyme.

In the treatment of chitosan with the chitosanase that is present in the culture fluid in which a suitable microorganism is grown, the hydrolysis of beta-1,4-D-glucosamic linkages will lead to a progressive reduction of the molecular weight of chitosan chains, decreasing chitosan viscosity and increasing its solubility in water. Various chitosan-related biological properties (immunostimulating activity in animals; elicitor activity of anti-pathogenic reactions in plants) are highly dependent of the average molecular weight.

STATEMENT OF THE INVENTION

It is a principal object of the present invention to provide a method of treating chitosan, preferably dissolved in an aqueous medium at moderately acidic pH, with a chitosanase for the purpose of hydrolysis of the beta-1,4-D-glucosaminic linkage in order to reduce progressively the molecular weight of the chitosan.

The invention also relates to a naturally occuring microorganism of the Actinomycete group, which has been isolated and characterized and which has been found to produce a new chitosanase, also an object of the present invention. The DNA sequence of the gene encoding this chitosanase as well as the amino acid sequence of the same have been elucidated, and are also under the scope of the invention.

It is a further object of the present invention to provide a recombinant microorganism of the Actinomycete group that is able of being cultured for the extracellular production of chitosanase.

Accordingly, in one aspect of the invention is provided a method of hydrolysing the beta-1,4-D-glucosaminic linkage within a chitinous substrate having chitosanase hydrolysable beta-1,4-D-glucosaminic linkages, said method comprising subjecting said material to said hydrolysis by a chitosanase obtained from the recombinant microorganism produced by the introduction of a hybrid plasmid into a host microorganism of the Actinomycete group, said hybrid plasmid being constructed by the insertion of the chitosanase gene (ohs) obtained from a chs gene-containing microorganism of the genus Streptomyces into a vector plasmid able to replicate into a microorganism of of the Actinomycete group, particularly of the genus Streptomyces. The chitosanase is secreted extracellularly into a culture medium of a recombinant microorganism in the presence of a suitable carbon source.

The chitosanase hydrolysable beta-1,4-D-glucosaminic linkage is within the chitosan (partially or totally N-deacetylated chitin) that is contained in the treated material. The enzymatic degradation of chitosan by hydrolysis of the beta-1,4-D-glucosaminic linkages is partial and thus there is not drastic release of D-glucosamine, N-acetyl-D-glucosamine, chitobiose or N-N-diacetyl-chitobiose. According to the present invention, the treatment of chitinous material, preferably dissolved in an aqueous medium at moderately acidic pH, by chitosanase results in progressive decrease of molecular weight, viscosity decrease and increase of water solubility.

In a further aspect, the invention provides a recombinant microorganism which contains a hybrid plasmid that carries a chs gene that codes for the production of chitosanase, wherein said plasmid is capable of inducing the extracellular secretion of chitosanase in a host microorganism into which said plasmid has been introduced. Preferably, the host microorganism is a strain of the Actinomycete group, preferably a strain of the genus Streptomyces. More preferably, the host microorganism is a mutant strain characterized by it having negative beta-1,4-D-glucosaminic linkages hydrolysing activity. Yet more preferably, the host microorganism is a strain characterized by it having naturally negative beta-1,4-D-glucosaminic linkages hydrolysing activity. Still yet more preferably, the host microorganism is a strain of the species *Streptomyces lividans* characterized by its negative beta-1,4-D-glucosaminic linkages hydrolysis activity. In yet a further aspect, the invention provides the hybrid plasmid constructed by the insertion of the chs gene into a vector plasmid. Preferably, the chs gene is obtained from microorganisms of the genus Streptomyces and the vector is a plasmid able to replicate into microorganisms of the Actinomycete group, particularly of the genus Streptomyces. More preferably, the chs gene is obtained from the strain Streptomyces N174 and/or the vector plasmid is pFD666 obtained from the strain *Streptomyces lividans* (pFD666) or the strain *Escherichia coli* (pFD666).

In a further aspect, the invention provides the recombinant microorganisms hereinabove defined for use in the production of chitosanase.

In yet a further aspect, the invention provides the hybrid plasmids hereinabove defined for use in the production of the recombinant microorganisms.

In still yet a further aspect, the invention provides the host microorganisms and the hybrid plasmids hereinabove defined for use in the production of the recombinant microorganisms.

In still yet a further aspect, the invention provides a method for the production of a recombinant microorganism hereinabove defined, comprising the introduction of a hybrid plasmid hereinabove defined into a host microorganism hereinabove defined.

The hybrid plasmid may be introduced into the host microorganism by the technique of protoplast fusion or more preferably by transduction or more preferably by transformation.

The chs gene is said to have been cloned upon its introduction into the host microorganism, hereinabove defined, thus providing a recombinant microorganism. The expression of the chs gene in the recombinant microorganism results in the production of chitosanase.

DETAILED DESCRIPTION OF THE INVENTION

The microorganism from which originates the cloned chitosanase is Streptomyces N174. This microorganism and the enzyme produced thereof have been isolated and characterized. The portion of the gene encoding the chitosanase has been isolated and cloned in suitable plasmidic vectors which led to the obtention of a recombinant strain of Streptomyces overexpressing the chitosanase. The present invention will be more readily understood by the following Examples and Figures which purpose is to illustrate rather than to limit the scope of the invention.

FIG. 1 represents the ratio polyacrylic acid/total extracellular proteins which achieves the best yield of chitosanase;

FIG. 2 represents the pH range activity of the chitosanase and the optimal temperature for the activity of the chitosanase for a 10 minute reaction at pH 5.5;

FIG. 3 shows the stability of the chitosanase in function of the temperature;

FIG. 5 represents the complete coding nucleic acid sequence and the deduced amino acid sequence of the chitosanase.

EXAMPLE 1

Microorganism and Culture Conditions

Figure 4:
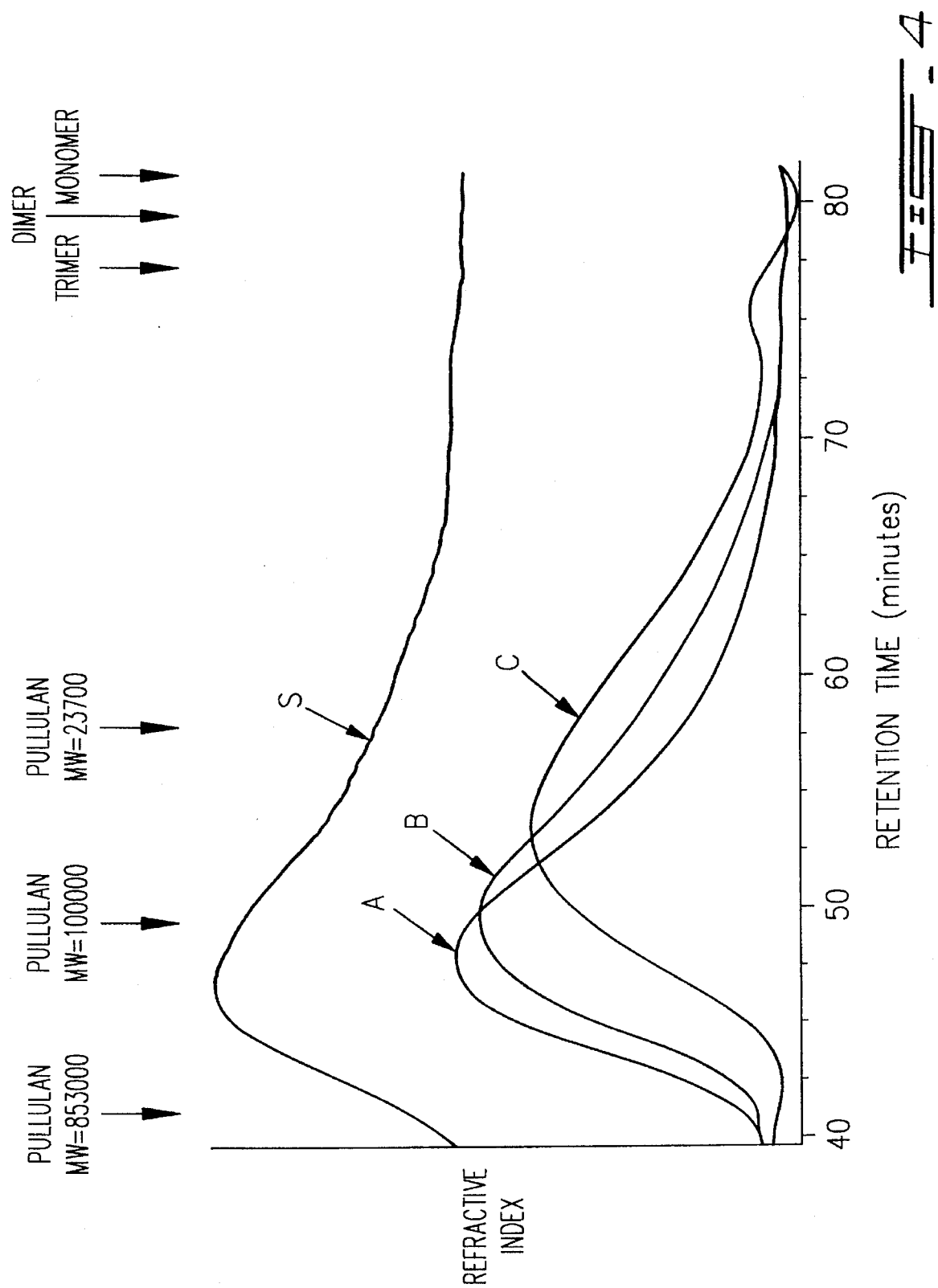
FIG. 4 represents the HPLC elution pattern of different molecular weight chitosans which are produced after a short reaction in presence of chitosanase.

In order to find microorganisms that secrete chitosan-degrading enzymes which could be used for biochemical and molecular studies as well as for large-scale production of chitosan oligomers, different types of soil were screened. Bacteria belonging to the Actinomycete group were retained for further studies, as they are known to be efficient producers of many extracellular enzymes (Peczynska-Czoch and Mordarski, 1988). The strain N174 was isolated from soil in a sugar maple grove near Sherbrooke (Quebec, Canada) using the following procedure: one gram of soil was added to 100 ml of liquid medium containing MS salts without $(NH_4)_2SO_4$ (Neugebauer et al., 1991) supplemented with 100 mg/l of peptone (Difco Lab., Detroit, Mich.) and 3.0 g/l of chitosan flakes (practical grade, Sigma Chemical Co., St-Louis, Mo.). The composition of the MS salt medium (Minimal Salts) is the following: 0.5 g of $MgSO_4$; 1.0 g of $(NH_4)_2SO_4$; 2.0 g of $K_2HPO_4$; 2.0 g of $KH_2PO_4$; 0.1 g of peptone; 0.01 g of $CaCl_2$, all dissolved in 1000 ml of distilled water, to which is added, after sterilization, 1 ml of a trace metal solution containing $CoCl_2.6H_2O$ (200 mg); $FeSO_4.7H_2O$ (500 mg); $MnSO4.H_2O$ (160 mg) and $ZnSO_4.7H_2O$ (140 mg), all dissolved in 100 ml of distilled water.

After 4 to 6 days of growth at 30° C., diluted portions of this selection culture were inoculated on Tryptic Soy Agar (Difco) plates. After different periods of growth, individual colonies with actinomycete-like morphology were tested for their ability to solubilize chitosan by transfer on chitosanase detection agar (CDA). CDA was prepared by mixing 15 g of agar, 300 ml of 1% chitosan (dissolved in 0.1M HCl) and 650 ml of distilled water containing the following salts: $(NH_4)_2SO_4$. 1.0 g; $MgSO_4.H_2O$, 0.5 g; NaCl, 1.0 g; $K_2HPO_4$, 0.5 g; $FeSO_4.7H_2O$, 0.01 g; $ZnCl_2$, 0.001 g; $CaCl_2.2H_2O$, 0.01 g; $MnCl_2$, 0.005 g). The pH was adjusted to 6.5 with 5M KOH and distilled water was added to 1 liter. The medium was sterilized for 15 minutes at 125° C. with constant stirring using a bench-top agar sterilizer (New Brunswick Scientific, Edison, N.J.), allowing the formation of a fine chitosan precipitate.

The strain was maintained on a sporulation medium (DeWitt, 1985) which composition is (per liter): starch 10 g, corn steep liquor 5 g, $CaCo_3$ 3 g, $FeSO_4$ 12 mg and agar 20 g (pH ajusted to 5.8 by addition of HCl). For chitosanase production, spores collected from an area of 10–15 cm² of the sporulation plate were used to inoculate 4 l flasks, each containing 800 ml of MS with 10 g/l of chitosan flakes, 0.2% olive oil (Bertrand et al., 1989) and 0.035% antifoam agent (Antifoam A, Sigma). Incubation was for 108 hours at 30° C. in a rotary shaker (model G25, New Brunswick Scientific) at 250 RPM. Mycelium was removed by filtration through a Schleicher and Schuell #410 filter.

The actinomycete Streptomyces N174 which has been deposited at the American Type Culture Collection Rockville, M.D. on Nov. 22, 1994, under accession number ATCC 55633, was selected as the most active chitosanase producer among 50 other Actinomycete isolates. It produces abundant aerial mycelium on Tryptic Soy Agar and sporulates well on the sporulation medium. Spores are formed in long chains.

The diaminopimelic acid form in the cell wall and the predominant sugar in whole-cell hydrolysates were analyzed by thin-layer chromatography according to Staneck and Roberts (1974). Mycolic acids were analyzed according to Tomiyasu and Yano (1984).

Meso-diaminopimelic acid is the predominant form in the cell walls of vegetative mycelium but the LL-form becomes predominant in spores. Galactose is the predominant sugar in whole-cell hydrolysates (arabinose was not detected). According to these data, the N174 strain was first classified in the genus Kitasatosporia (Omura et al., 1982). However, recently, the whole genus Kitasatosporia has been transferred to the genus Streptomyces (Wellington et al., 1992). Thus the N174 strain is referred as Streptomyces N174. Other characteristics of this strain are listed in Table 1.

TABLE 1

| CHARACTERISTICS OF THE STRAIN N174 | |
| --- | --- |
| Composition of phospholipids PII pattern (Le Chevalier et al.) | (absence of phosphatidyl choline and of phosphatidyl glycerol |
| Utilisation of sugars | |
| raffinose | + |
| arabinose | + |
| mannitol | + |
| rhamnose | + |
| saccharose | + |
| fructose | + |
| xylose | + |
| glucose | + |
| No production of melanine | |
| No growth in presence of violet crystal | 0.001% |
| Sensitivity to neomycine | (50 µg/ml) |
| Resistance to streptomycine | (50 µg/ml) |

EXAMPLE 2

Chitosanase Produced By N174

The best results for chitosanase production by N174 were obtained in a medium containing chitosan as sole carbon source. Various enrichments (0.5% peptone; 0.5% casamino acids; 1% starch) increased growth rate but decreased chitosanase production to, respectively, 5–10%, 5–10% and 20–50% of the levels obtained with chitosan. 0.5% D-glucosamine as sole carbon source also induced chitosanase production but at levels reaching only 15–25% of those obtained in chitosan medium. EXAMPLE 3

Enzyme Purification

The culture filtrate (total volume 1.5 l) was cooled to 4° C. (this temperature was maintained throughout the purification procedure) and adjusted to pH 4.5 with 5M acetic acid. Chitosanase was precipitated following a modification of the procedure of Sternberg and Hershberger (1974): a 2% (w/v) solution of polyacrylic acid (average molecular weight 250,000, Aldrich Chem. Co., Milwaukee, Wis.) was added dropwise to a final proportion of 4 mg per mg of extracellular proteins. After 30 minutes of mixing, the precipitate was collected by centrifugation (11,000×g; 30 minutes) and resuspended in 300 ml of distilled water. NaOH 1M was added until pH raised to 8.5. In order to remove the residual polyacrylic acid, a 1M solution of calcium acetate was added dropwise (final concentration: 35 mM) and the precipitate was removed by centrifugation and discarded. The supernatant was acidified down to pH 5.0 with 1M acetic acid.

The acidified supernatant was applied to a an ion exchange column, for instance a 1.6×38 cm S-Sepharose Fast Flow column (Pharmacia LKB, Baie d'Urfé, Québec) previously equilibrated with buffer A (25 mM Na-acetate buffer, pH 4.5). The flow rate was 70 ml/h. 5 ml fractions were collected. Unbound protein was washed from the column with 50 ml of buffer A, then a linear 300 ml gradient from 0 to 0.6M NaCl in Buffer A was applied. Fractions containing the chitosanase activity were identified by spotting 10 µl of each fraction on CDA plates and incubating for 4 hours at 45° C. The active fractions (total volume 45 ml) were pooled and concentrated 6 times by techniques well known in the art, for instance by overnight dialysis against Bio-Gel Concentrator Resin (Bio-Rad, Richmond, Calif.)

The concentrated sample was made 20% glycerol and applied on a 1.6×98 cm column packed with Bio-Gel A-0.5 m (200–400 mesh; Bio-Rad) equilibrated with Buffer A under gravity pressure. In the same buffer, flow rate was 15 ml/h. 2.5 ml fractions were collected. Active fractions were identified as before and analyzed by SDS-PAGE. The purified chitosanase was stored at −20° C. after addition of 1 volume of sterile glycerol. Under these conditions, the enzyme was stable for many months.

Various procedures for the isolation and the concentration of the enzyme were attempted: precipitation with acetone, ethanol, ammonium sulfate and polyethylene glycol 3350. For unknown reasons, none was satisfactory, resulting in significant loss of enzyme activity. Having established that the N174 chitosanase has a slightly alkaline pI (Fink et al., 1991), polyacrylic acid, a precipitant used in large-scale preparations of some industrial enzymes (Sternberg and Hershberger, 1974) was successfully tried. Direct addition of polyacrylic acid solution to the culture supernatant (which pH varied from 5.8 to 6.5 in different experiments) gave relatively low enzyme recoveries (25–55%). Acidification of the culture supernatant with 1M acetic acid (down to pH 4.5) before polyacrylic acid addition resulted in better enzyme recoveries (around 85%). The optimal ratio polyacrylic acid/total extracellular proteins was found to be around 4 (FIG. 1).

After two subsequent chromatographic steps using the same procedure as above, a chitosanase was obtained, homogeneous as estimated from polyacrylamide gels stained with Coomassie Blue and from $NH_2$-terminal amino acid sequencing and having a specific activity of 59.8 units per mg of protein.

EXAMPLE 4

Enzyme Assays

Chitosanase activity standard assay contained 950 µl of 0.2% chitosan solution in 50 mM acetate buffer pH 5.5, 1 to 20 mU of enzyme and water to a final volume of 1.0 ml. Incubation was for 10 minutes at 37° C. The reaction was terminated by addition of 300 µl of the reaction mixture to 1.2 ml of the neocuproine reagent (Dygert et al., 1965). After 15 minutes of incubation at 100° C. in a mineral oil bath, chilling under tap water, dilution with 1.5 ml of distilled water and centrifugation in a table-top centrifuge (in order to eliminate the chitosan precipitate), soluble reducing sugars were measured spectrophotometrically at 450 nm. One unit of enzyme was defined as the amount that liberated 1 µmol of D-glucosamine equivalent in 1 minute under the above conditions.

EXAMPLE 5

Enzyme Substrates

Chitosan (practical grade, C-0792, Sigma) was used for standard chitosanase assays. Its degree of acetylation (d.a.) was 21%. Chitosan A and B (d.a. of 61% and 54%, respectively) were prepared by acetylation of chitosan Sigma with acetic anhydride according to Hirano and Ohe (1975). Chitosan C (d.a. 43%) and D (d.a. 34%) were obtained by a thermo-mechano-chemical treatment (Pelletier et al., 1990). Chitosan E (d.a. 1%) was prepared by deacetylation of chitosan Sigma by the procedure of Domard and Rinaudo (1983). Chitosan F (d.a. 1%) was from Katakura Chikkarin Co., Japan and was a gift of Dr Kusaoke.

All chitosans were prepared as 10 mg/ml stock solutions in 0.25M acetate buffer (pH 5.5). Chitosans C and D were only partially soluble and enzymatic assays were carried out using their soluble fraction.

Other substrates like glycol chitosan, carboxymethyl cellulose, purified chitin and laminarin were from Sigma. Colloidal chitin was prepared using the procedure of Hsu and Lockwood (1975). Avicell was purchased from FMC Co. (Philadelphia, Pa.).

The purified enzyme was specific for chitosan degradation. No hydrolysis of colloidal chitin, purified chitin, CM-cellulose, Avicell, laminarin, N-N-diacetylchitobiose, p-nitrophenyl-β-D-N-acetylglucasaminide or p-nitrophenyl-β-D-glucosaminide was observed. The relationship between enzyme activity and the degree of acetylation of the chitosan substrate was tested on a series of chitosans prepared by various chemical methods. Maximal rates of hydrolysis was observed for chitosans with low degrees of acetylation (1–21%: chitosans E,E and Sigma) but the N174 chitosanase was able to hydrolyse efficiently chitosans in the range of d.a. from 34 to 61%, exhibiting still half of the maximal hydrolysis rate against the most acetylated of these substrates, chitosan A (d.a. 61%). Glycol chitosan was hydrolysed at 35% of the maximal rate.

EXAMPLE 6

Analytical Procedures

Protein concentration was estimated by the method of Stoscheck (1990) with bovine serum albumin as standard. The $NH_2$-terminal protein sequence was determined by Edman degradation with an Applied Biosystems 473A protein sequencer. Thin-layer chromatography of end products of chitosan degradation was performed as described (Neugebauer et al., 1991). The system used for analytical high-performance size-exclusion chromatography consisted of a Waters 590 pump, a WISP 512 automatic injector and a Waters 410 refractive index detector. Two TSK gel columns in series (600×7.5 mm) thermostated at 25° C. were employed: G3000PW and G4000PW (Toso Haas, Philadelphia, Pa.). The effluent, degassed and filtered (0.45 µm) 2% acetic acid with sodium nitrate (0.2M) and sodium azide (0.1%), was pumped at 0.5 ml/minute. The samples from enzymatic digestions were filtered (0.45 µm) and 50 µl were injected (in some cases the samples had to be diluted in order to keep the dissolved solids concentration under 4 mg/ml). All the data were acquired and processed with the aid of the Waters Maxima 820 software program (Millipore Waters, Mississauga, Ontario).

The $NH_2$-terminal sequence of the purified enzyme was determined to be Ala-Gly-Ala-Gly-Leu-Asp-Asp-Pro-His-Lys-Lys-Glu-Ile-Ala-Met-Glu-Leu-(SEQ ID NO: 1). Previously, the $M_r$ of the purified enzyme was estimated to be approximately 29500 by SDS-polyacrylamide gel electrophoresis (Fink et al., 1991).

Optimal reaction conditions, enzyme stability and kinetic parameters were determined with chitosan Sigma as the substrate. The pH range for activity extended from 4.0 to 6.0 with a maximum at 5.5 (FIG. 2). A sharp drop in activity was observed at pH values higher than 6.5 coinciding with precipitation of the substrate. The enzyme was stable in a pH range of 4.5 to 6.0 for at least 4 hours at 37° C.

The optimal temperature for a 10 minute reaction at pH 5.5 was about 65° C. (FIG. 2).

The apparent $K_m$ determined from a single reciprocal plot (not shown) was 0.088 mg/ml and $V_{max}$ was 96.6 U/mg. Substrate inhibition was observed at chitosan concentrations higher than 1 mg/ml.

Thermal stability of the chitosanase was determined by incubating the enzyme in 50 mM acetate buffer pH 5.5 at various temperatures and for various periods of time in the absence of chitosan, after which the residual activity was determined by the standard assay. The enzyme was stable at 37° C. but its stability decreased rapidly above 40° C. (FIG. 3). As described for chitosanase A from *Bacillus megaterium* P1 (Pelletier and Sygusch, 1990b), stability could be improved by addition of 0.1 mg/ml of bovine serum albumin to the preincubation buffer. These studies showed, however, that the enzyme is relatively thermolabile. Therefore, for periods of incubation longer than 10 minutes, a temperature not higher than 40° C. should be used in order to insure the stability of the chitosanase.

HPLC analysis of products obtained from the early stages of reaction showed a rapid decrease of molecular weight of the chitosan substrate (FIG. 4), indicating that the enzyme hydrolyses chitosan in an endowise manner. The products of a complete digestion of chitosan were analyzed by thin-layer chromatography (not shown). As for other chitosanases (Price and Storck, 1975; Pelletier and Sygusch, 1990b), the main products detected were dimers and trimers of D-glucosamine with only traces of free D-glucosamine or higher oligomers. Thus, the tetramer should be the shortest oligomer still recognized as a substrate by the chitosanase.

In many respects, the Streptomyces N174 chitosanase, described herein, resembles that of Streptomyces sp. No 6 (Price and Storck, 1975). Both enzymes cannot be precipitated from culture filtrates by conventional laboratory techniques, both exhibit the same mechanism of chitosan hydrolysis, they do not attack chitin and CM-cellulose and they have similar molecular weights. The pI of Streptomyces sp. No 6 chitosanase was not determined, but can be deduced as being near to neutral from its behaviour in ion exchange chromatography, thus it is similar to that of N174 chitosanase. The Streptomyces sp. No 6 has however a much higher apparent $K_m$ for chitosan compared with that of N174, suggesting that there are significant differences between the two enzymes.

The strain Streptomyces N174 is one of the most efficient producers of chitosanase described so far in the litterature. In filtrates obtained after cultivation of N174 in chitosanase production medium, the chitosanase accounts for approximately 50–60% of total extracellular proteins. Precipitation with polyacrylic acid, an easy and inexpensive step, gives enzyme preparations with a chitosanase specific activity reaching 72–75% of that of the purified enzyme. This enzyme preparation is stable for many weeks at 4° C. and does not contain other chitino- or chitosano-lytic activities (data not presented). Thus, the N174 strain is suitable for large scale chitosanase production (in the hundreds of milligrams or the grams range).

EXAMPLE 7

Obtention of Recombinant Plasmid and Recombinant Microorganism

Even if N174 is an excellent producer of chitosanase, the yield of chitosanase can be greatly increased by using DNA recombinant techniques.

The recombinant microorganism of the present invention contains a hybrid plasmid that carried the chs gene that codes for the production of chitosanase. The hybrid plasmid can be constructed by any conventional methods for the insertion of required DNA fragment (chs gene) into a vector plasmid. Preferably, chromosomal DNA is extracted from the above-described Streptomyces N174 according to Chater et al. (1982). Plasmid DNA was purified from the strain *Streptomyces lividans* TK24 (obtained from D. A. Hopwood (John Innes Institute, Norwich, UK) as described by Kieser (1984). For the gene bank construction, 3 µg of vector pIJ702 DNA (Katz et al., 1983) cut with BglII and dephosphorylated using a heat-labile phosphatase (Bio/Can Sc., Mississauga, Ontario, Canada) were ligated to 5 µg of a total BglII digest of N174. After ligation, DNA was transformed into TK24 protoplasts following the procedure of Hopwood et al. (1985). 12500 transformants were recovered on R2YE regeneration medium containing 50 µg/ml of thiostrepton (courtesy of Squibb & Sons Ltd, Montreal, Canada). From these transformants, approximately 9000 were melanin-negative, indicating the presence of an insert at the BglII site of the vector pIJ702. The transformants were transfered by replica plating on CDA plates. On this medium, the strain TK24 gave a faint solubilization of chitosan after 4 to 5 days of growth (owing to chitinolytic activities produced by this strain (Neugebauer et al., 1991). The clone pDF22 carrying an insert of 6.5 kb was selected.

In order to localize the chs gene, a plasmid was constructed by sub-cloning the 6.5 kb BglII fragment of pDF22 into the BamHI site (dephosphorylated) of the shuttle vector pFD666, which is able to replicate in Streptomyces and *E. coli* (Denis and Brzezinski, 1992). This plasmid has the origin of replication of ColE1 for propagation in *E. coli*, the origin of replication of pJV1 (Bailey et al., 1986) for propagation in Actinomycetes, more particularly in Streptomyces and a modified aminoglycoside resistance gene (Denis and Brzezinski, 1991). The vector pFD666 is obtained from *Escherichia coli* (pFD666), a culture of which is on deposit at the National Collection of Industrial and Marine Bacteria Limited, Aberdeen, UK under Accession number NCIMB 13218, and at the American Type Culture Collection under Accession number 77286. Donor and plasmid DNA were mixed at a ratio 3:1 (w:w), ligated using 0.5 unit of T4 DNA ligase for 4 hours at room temperature at a concentration of 80 µg/ml.

After transformation, a chitosanase-producing clone was selected and designated *Streptomyces lividans* (pDF220). The plasmid pDF220 extracted from this clone carried the DNA insert of 6.5 kb (kilobase pairs). When cultured in liquid medium (as described in Example 1), this clone was found to produce a chitosanase which $M_r$ was identical to that of the chitosanase produced by the DNA donor strain Streptomyces N174. The host strain transformed with the vector pFD666 did not produce any significant chitosanase activity in the same conditions. Various intraplasmidic deletions were produced by total or partial restriction enzyme digestion and by intramolecular ligation, giving plasmids pDF221 to 225 (FIG. 5). Other deletions were produced directly in the pDF22 plasmid, giving the pDF22-11 and pDF22-5 plasmids (FIG. 5). After transformation into TK24, the shortest segment of this series examined (that of the pDF225 plasmid) still gave an intense solubilization of chitosan.

The DNA of the hybrid plasmid pDF220 was digested with the restriction endonuclease PstI and a DNA fragment of 2.6 kb containing the chitosanase (chs) gene was subcloned by ligation with the pFD666 plasmid vector digested with the PstI enzyme.

The recombinant microorganism is produced by the introduction of the hybrid plasmid (ligation product) into a host microorganism strain of the genus Streptomyces, preferably a microorganism lacking beta-1,4-glucosaminic linkage hydrolysing activity. A suitable host, *Streptomyces lividans* 1326 is available from the National Collection of Industrial and Marine Bacteria limited, Aberdeen, U.K. under Accession number NCIMB 40257. A chitosanase-positive clone obtained after transformation of *Streptomyces lividans* 1326 was selected and designated *Streptomyces lividans* (pRL226).

The extracellular chitosanase produced by the recombinant strain *Streptomyces lividans* (pRL226) was purified to homogeneity. The purified enzyme has an apparent $M_r$ of 29,000 daltons and pI of 7.5. This $M_r$ value corresponds exactly to the $M_r$ value of the native purified chitosanase from Streptomyces N174. The chitosanase produced by *Streptomyces lividans* (pRL226) showed no activity towards chitin and N-N-diacetylchitobiose. The enzyme degrades chitosan, producing mainly chitobiose and a mixture of oligomers of D-glucosamine as end products. The level of chitosanase production in the original Streptomyces N174 was approximately 5 IU/ml of culture supernatant. After cloning, the level of production reached approximately 35 IU/ml of supernatant.

The expression of the chitosanase gene varies according to the source of carbon used in the culture medium. The chitosanase was produced by *Streptomyces lividans* (pRL226) in culture medium containing 2% tryptic soy broth or starch or malt extract as main carbon sources. Preferably the carbon source in the growth medium is 1.5% of chitosan flakes and 0.5% malt extract or 1.5% of chitosan flakes and 0.5% starch. Yet more preferably the carbon source in the medium consists in 3% of dry sterile mycelium of a mould of the genus Mucor or Rhizopus. In the last-mentioned medium, *Streptomyces lividans* (pRL226) produces chitosanase at a concentration of 95 IU/ml.

Further, in accordance with the method of the present invention, a chitosan solution in an aqueous medium at moderately acidic pH is treated with chitosanase. While it is preferred to employ solubilized chitosan, other insoluble chitosan forms may be used. The chitosan is treated with chitosanase contained in the supernatant of a recombinant *Streptomyces lividans* clone. The enzyme solution can be purified and/or concentrated using the above-described biochemical techniques. The chitosanase is used at a concentration ranging from 0.001 to about 10 IU/ml and at a temperature of from 20° C. to about 80° C., preferably about 40° C. The chitosan concentration is from about 0.1% to about 4%, based on the dry weight. A concentration of about 0.5% to 2% is preferred. The mixture can be mixed with the use of mixing devices. The chitosanase action can be inhibited by heating the reaction mixture to about 90° C. for the required amount of time. The depolymerized chitosan is then used depending upon the type of product desired.

EXAMPLE 9

Production of Chitosanase and Degradation of Chitosan by the Recombinant Strain *Streptomyces Lividans* (pRL226)

The ability of chitosanase production of the various strains was studied by cultures in liquid media. In all tests, the Minimal Salts (MS) medium was used. For chitosanase production tests, a medium containing MS salts supplemented with 10 g/l of chitosan flakes (practical grade; Sigma Chemical Co., St. Louis, Mich. U.S.A.) was used. Cultures were incubated at 30° C. Production levels are shown in Table 2.

TABLE 2

| Strain | Chitosanase activity in IU/ml* |
|---|---|
| S. lividans 1326 | 0.02 |
| S. lividans (pFD666) | 0.02 |
| S. lividans (pDF220) | 35.5 |
| S. lividans (pRL226) | 38.8 |

(*): Chitosanase activity was measured by incubating 0.05 ml of enzyme solution (diluted, if necessary, in 0.1M Na-acetate buffer, pH 5.5) with 0.95 ml of 1% chitosan in the same buffer, at 37° C. for 10 minutes. Reaction was terminated by addition of the neocuproine reagent and heating for 15 min in an oil bath at 105° C.. Reducing sugars were determined with D-glucosamine as standard.

The culture supernatant concentrates of all the strains described in Table 2 were analyzed for secreted chitosanase by SDS-polyacrylamide gel electrophoresis. The chitosanase produced by the strains *S. lividans* (pDF220) and *S. lividans* (pRL226) had identical electrophoretic mobility as the purified chitosanase of the original strain Streptomyces N174. This was further confirmed by comparison of biochemical properties such as pI, pH and temperature optima.

The expression of the chitosanase gene varied according to the carbon source present in the medium. While some production was observed in absence of chitosan, on media such a MS+2% malt extract (Difco Lab, Detroit, Mich., U.S.A.) or MS+2% starch (potato starch powder; Anachemia Canada Inc., Montreal); production was significantly enhanced on chitosan containing media, in which the content of malt extract or starch was reduced to 0.5%. Table 3 shows the level of chitosanase production in some media, obtained with the strain *Streptomyces lividans* (pRL226).

TABLE 3

| | Chitasanase activity (UI/ml) | |
|---|---|---|
| Medium composition | 72 h | 120 h |
| MS + 1.5% chitosan + 0.5% starch | 48.8 | 19.5 |
| MS + 1.5% chitosan + 0.5% malt extract | 50.3 | 24.0 |
| MS + 2% malt extract | 6.6 | 11.8 |
| MS + 2% starch | 4.9 | 10.0 |

Table 4 shows a comparison of enzyme production by *Streptomyces lividans* (pRL226) on media with various natural substrates containing chitin or chitosan. Sterile and dry cells and/or mycelia of various fungal microorganisms were included at a final concentration of 3% (dry weight) into the production medium. The highest chitosanase levels were obtained with dry sterile mycelia of two chitosan-containing microorganisms, *Mucor rouxii* and *Rhizopus oryzae*, requiring, however, a significantly longer fermentation period of 7–8 days.

TABLE 4

| | Chitosanase activity (UI/ml) | | |
|---|---|---|---|
| Medium composition | 96 h | 144 h | 192 h |
| MS + 3% of dry cells of *Saccharomyces cerevisiae* | 18.2 | 21.5 | 22.3 |
| MS + 3% of dry mycelium of *Aspergillus niger* | 26.2 | 29.0 | 27.7 |

TABLE 4-continued

| | Chitosanase activity (UI/ml) | | |
|---|---|---|---|
| Medium composition | 96 h | 144 h | 192 h |
| MS + 3% of dry mycelium of Rhizopus oryzae | 32.5 | 45.2 | 48.9 |
| MS + 3% of dry mycelium of Mucor rouxii | 67.5 | 70.3 | 94.8 |

The results shown in Tables 3 and 4 stress out an interesting point. Depending on the substrate used, the time chosen for measuring chitosanase activity is of importance. Upon different substrates, the cells reach a stationnary growth phase more or less rapidly. Proteasic activities develop when the cells attain this stationnary phase. This could explain why different substrates show different maximal chitosanase activities at different times because these proteasic activities were shown to degrade the chitosanase, when they develop in the medium.

A supernatant of a recombinant *Streptomyces lividans* (pRL226) clone containing the chitosanase enzyme assayed at approximately 60 IU/ml at a protein concentration of approximately 1.4 mg/ml (Bradford assay) was further purified. The supernatant containing the enzyme was acidified with acetic acid down to pH 4.5 and a 2% (w/v) solution of polyacrylic acid (average molecular weight 150,000; Aldrich Chem. Co., Milwaukee, Wis.) was added dropwise to a final proportion of 4 mg per mg of extracellular proteins. After 30 minutes of mixing, the precipitate was collected by filtration and resuspended in 1/5 of the original supernatant volume of distilled water. 1M NaOH was added until pH raised to 8.5. In order to remove the residual polyacrylic acid, a 1M solution of calcium acetate (final concentration: 35 mM) was added dropwise and the precipitate was removed by filtration and discarded. The supernatant was acidified down to pH 5 with acetic acid. This crude enzyme preparation was kept at 4° C. until used. This precipitation step eliminates about 95% of proteasic activity which is not precipitated with polyacrylic acid. This further explain the good stability of the so purified enzyme which is now substantially free of proteases.

A chitosan sample used in this test was dissolved in 1M acetic acid and diluted up to a final concentration of 4 mg/ml with 50 mM sodium acetate pH 5.5. Treated and control samples (1 g of each) were incubated at 37° C. The treated samples had various amounts of crude chitosanase preparation added to them for a final activity of 0.006–0.2 IU/ml, for 10 minutes of incubation with constant mixing. Once the incubation completed, control and treated samples were boiled for 10 minutes in order to inactivate the enzyme. The average degree of polymerization of chitosan in various samples was determined by high-performance liquid chromatography (HPLC). The results are listed in Table 5. A progressive decrease of the chitosan molecular weight was obtained.

TABLE 5

| Chitosanase activity in sample | Average degree of polymerisation of chitosan at the end of treatment |
|---|---|
| No enzyme (control sample) | 2750 |
| 0.006 IU/ml | 1000 |
| 0.013 IU/ml | 450 |
| 0.025 IU/ml | 200 |
| 0.050 IU/ml | 90 |
| 0.10 IU/ml | 30 |
| 0.20 IU/ml | 8 |

EXAMPLE 10

Sequencing and Mapping of the Gene Encoding Chitosanase

For sequencing purposes, the DNA segment containing the chs gene and some flanking sequences was obtained by digesting plasmid pRL226 by the restriction endonuclease PstI, separating this segment on agarose gel and extracting it thereof, and ligated in plasmid pUC119 (Vieira and Messing, 1987) digested by the same restriction enzyme. The ligated product was used to transform *E. coli* DH5α cells. Clones having a recombinant plasmid bearing the inserted DNA segment, in both directions were retained.

A series of nested deletions was generated using the exonuclease III/S1-nuclease procedure (Hennikoff, 1984). The sequence of a 1575 nucleotide BamHI-PstI segment was determined on both strands using the dideoxy method (Sanger et al., 1977). The 5'-GTAAAACGACGGCCAGT-3' (SEQ ID No. 4) oligonucleotide (obtained from New England Biolabs, Beverly, Mass.) was used as a sequencing primer.

The nucleic acid sequence and the amino acid sequence obtained are represented in FIG. 5.

All the restriction enzyme sites first mapped using the recombinant pUC119 and using standard and well known procedures (Fink et al., 1991) have been confirmed by the sequence obtained (SEQ ID No. 2). The open-reading frame (ORF) corresponding to the chitosanase starts at nucleotide 225 and ends at nucleotide 1058. This ORF determines a protein of 278 amino acids (SEQ ID No: 3). The N-terminal amino acid sequence of the purified extracellular chitosanase has shown that the mature enzyme starts at the amino acid 41 (Ala-Gly-Ala-Gly . . . ). The first forty amino acids (corresponding to the amino acids encoded by nucleotides 225 to 344) act as a signal peptide sequence (Von Heijne, 1990) and are necessary for the secretion of the chitosanase outside the bacterial cell.

The calculated molecular weight of the chitosanase does not correspond to that measured on SDS-polyacrylamide gel. This discrepancy might be explained by the two putative glycosylation sites beared by the chitosanase or, by the non-globular conformation which could be adopted by the chitosanase, conferring retardation of migration on SDS-polyacrylamide gel and engendering an over-evaluation of its molecular weight. These hypotheses are under investigation.

REFERENCES

Bailey, C. R., et al. (1986). J. Gen. Microbiol. 132: 2071–2078

Bertrand, J.-L., et al. (1989) "Expression of the xylanase gene of *Streptomyces lividans* and production of the enzyme on natural substrates". Biotechnol. Bioeng. 33: 791–794

Chater, et al. (1982). Curr. Topics Microbiol. Immunol. 97: 69

Denis, F. et al. (1992). Gene 111: 115

Denis, F., et al. (1991). FEMS Microbiol. Lett. 81:261–264

De Witt, J. P. et al. (1985). "Evidence for fex factor in *Streptomyces erythraeus*. J. Bacteriol. 164: 969–971

Domard, A., et al. (1983). "Preparation and characterization of fully deacetylated chitosan". Int. J. Biol. Macromol. 5:49–52

Fenton, D. M., et al. (1981). "Purification and mode of action of a chitosanase form *Penicillium islandicum*". J. Gen. Microbiol. 126:151–156

Fink, et al. (1991). Biotechnology Letters. 13(12): 845

Hirano, S., et al. (1975) "A facile N-acylation of chitosan with carboxylic anhydrides in acidic solutions". Carbohydro. Res. 41: C1–C2

Hopwood, D. A., et al. (1985). *Genetic manupulation of Streptomyces—a laboratory manual*. John Innes Foundation, Norwich Horowitz, S. T. et al. (1957). Journal of American Chemical Society 79: 5046

Hsu, S. C., et al. (1975) "Powdered chitin agar as a selective medium for enumeration of actinomycetes in water and soil". Appl. microbiol. 29: 422–426

Katz, E. et al. (1983). J. Gen. Microbiol. 129: 2703–2714

Kieser, T. (1984). Plasmid 12: 19–36

Nanjo, F. et al. (1990). "Purification and characterization of an exo-β-D-glucosaminidase, a novel type of enzyme, from *Nocardia orientalis*". J. Biol. Chem. 265: 10088–10094

Neugebauer, E. et al. (1991). "Chitinolytic properties of *Streptomyces lividans*, Arch. Microbiol. 156: 192–197

Omura, S. et al. (1982). "Kitasatosporia, a new genus of the order Actinomycetales". J. Antibiotics. 35: 1013–1019

Peczynska-Czoch, W. P. et al. (1988). "Actinomycete enzyme" In Goodfellow, M. et al. (Eds). *Actinomycetes in biotechnology*. Academic Press. New York. pp. 219–283

Pelletier, A. et al. (1990a). "Chitin/chitosan transformation by thermo-mechano-chemical treatment including characterization by enzymatic depolymerization". Biotechol. Bioeng. 36: 310–315

Pelletier, A. et al. (1990b) "Purification and characterization of three chitosonase activities from *Bacillus megaterium* P1". Appl. Environ. Microbiol. 56:844–848

Price, J. S. et al. 1975). "Production, purification and characterization of an extracellular chitosane from Streptomyces". J. Bacteriol. 124: 1574–1585

Sakai, K., et al. (1991). "Purification and hydrolytic action of chitosanase from *Norcardia orientalis*". Biochim. Biophys. Acta 1079: 65–72

Sandford, P. A. (1989). In Skjak-Braek, G. et al. (Eds). Chitin and Chitosan Elsevier Applied Science. pp. 51–70

Staneck, J. L. et al. (1974). "Simplified approach to identification of aerobic actinomycetes by thin-layer chromatography". Appl. Microbiol. 28: 226–231

Sternberg, M., et al. (1974). "Separation of proteins with polyacrylic acids". Biochim. Biophys. Acta 342:195–206

Stoscheck, C. M. (1990) "Increased uniformity in the response of the Coomassie Blue G protein assay to different proteins". Anal. Biochem. 184: 111–116

Tomiyasu, I., et al. (1984). "Separation and analysis of novel polyunsaturated mycolic acids from a psychrophilic, acid-fact bacterium, *Gordona aurantiaca*". Eur. J. Biochem. 139: 173–180

Wellington, E. M. H., et al. (1992). "Taxonomic status of Kitasatosporia, and proposed unification with Streptomyces on the basis of phenotypic and 16S rRNA analysis and emendation of Streptomyces". Waksman and Henrici 1943, 339$^{AL}$. Int. J. Syst. Bacteriol. 42: 156–160

Yabuki, M. et al. (1988). "Purification and properties of chitosanase from *Bacillus circulans* MH-K1". J. Gen. Appl. Microbiol. 34: 255–270

---

What is claimed is:

1. A chitosanase isolated from Streptomyces N174 or obtained from a microorganism of the genus Streptomyces which produces said chitosanase, the chitosanase hydrolysing specifically a substrate chitosan, said chitosanase having the following characteristics:

an apparent molecular weight ($M_r$) of 29500 kilodaltons measured by SDS-polyacrylamide gel electrophoresis;

a pH range for activity extending from 4.0 to 6.0, with a maximum of activity at pH 5.5;

an apparent constant of affinity ($k_m$) for said substrate chitosan of 0.088 mg/ml and a maximal velocity of hydrolysis ($V_{max}$) of 96.6 U/mg, where in U is defined as the amount of chitosanase that liberates 1 µmol of the product of said hydrolysis, D-glucosamine equivalent, in one minute of enzymatic reaction at 37° C. in a one ml volume of reaction containing 50 mM acetate buffer pH 5.5 and 0.2% solubilized chitosan having a degree of acetylation of 21%, the reaction of said substrate with said chitosanase being allowed for 10 minutes and stopped by addition of neocuproine reagent.

2. A chitosanase according to claim 1, having the amino acid sequence defined in SEQ. ID. No. 3.

3. A method of production of chitosanase as claimed in claim 1, comprising the following steps:

culturing a strain producing said chitosanase in a culture medium containing a carbon source which is able to support growth of said strain and production of chitosanase;

recovering said chitosanase secreted in said culture medium; and purifying said chitosanase by adding a solution of polyacrylic acid to said medium which precipitates said chitosanase.

4. A method according to claim 3 wherein the solution of polyacrylic acid has a concentration of 2% and said solution is added till the weight of polyacrylic reaches 4 times the weight of proteins measured in said medium.

5. A method according to claim 3 further characterized by a further purification of said chitosanase by chromatography, said further purification achieving a substantially pure chitosanase.

6. A method according to any one of claims 3 to 5 wherein the strain is Streptomyces N174 having ATCC Deposit Number 55633.

7. A method of hydrolysis of chitosan by chitosanase which comprises the following steps:

adding the chitosanase of claim 2 to a solution containing chitosan;

allowing hydrolysis to occur;

detecting said hydrolysis by measuring the average degree of polymerization of said chitosan.

8. A method according to claim 7 wherein said degree of polymerization is measured by HPLC.

9. A method according to claim 7 wherein said chitosanase and chitosan are mixed in the proportions of 0.006 to 0.2 IU/ml and 0.1 to 4 mg/ml, respectively in a 50 mM sodium acetate buffer, pH 5.5.

* * * * *